United States Patent [19]

Johnson et al.

[11] Patent Number: 5,623,323
[45] Date of Patent: Apr. 22, 1997

[54] EXTRA WIDE FIELD OPHTHALMIC LENS

[75] Inventors: Robert D. Johnson; Janet L. Crossman, both of Bellevue, Wash.; Martin A. Mainster, Leawood, Kans.

[73] Assignee: Ocular Instruments, Inc., Bellevue, Wash.

[21] Appl. No.: 329,712

[22] Filed: Oct. 26, 1994

[51] Int. Cl.⁶ ............................ A61B 3/00; G02C 7/04
[52] U.S. Cl. ..................................... 351/219; 351/160 R
[58] Field of Search ................................ 351/219, 247, 351/160 R

[56] References Cited

U.S. PATENT DOCUMENTS

| | | | |
|---|---|---|---|
| 3,770,342 | 11/1973 | Dudragne | 351/7 |
| 3,820,879 | 6/1974 | Frisen | 351/1 |
| 3,954,329 | 5/1976 | Pomerantzeff | 351/16 |
| 4,023,189 | 5/1977 | Govignon | 354/62 |
| 4,027,952 | 6/1977 | Hugues | 350/189 |
| 4,134,647 | 1/1979 | Ramos-Caldera | 351/6 |
| 4,222,634 | 9/1980 | Muchel | 350/189 |
| 4,265,519 | 5/1981 | Pomerantzeff | 351/16 |
| 4,357,088 | 11/1982 | Pomerantzeff | 354/62 |
| 4,410,245 | 10/1983 | Koester | 351/219 |
| 4,452,514 | 6/1984 | Spitznas | 351/206 |
| 4,469,413 | 9/1984 | Shirayanagi | 350/432 |
| 4,502,764 | 3/1985 | Riquin | 351/160 R |
| 4,627,694 | 12/1986 | Volk | 351/214 |
| 4,637,699 | 1/1987 | Sigelman | 351/205 |
| 4,669,839 | 6/1987 | Muchel | 351/221 |
| 4,671,631 | 6/1987 | Sigelman | 351/205 |
| 4,682,866 | 7/1987 | Volk | 351/205 |
| 4,704,018 | 11/1987 | Takahashi | 351/206 |
| 4,721,378 | 1/1988 | Volk | 351/205 |
| 4,728,183 | 3/1988 | Heacock et al. | 351/219 |
| 4,738,521 | 4/1988 | Volk | 351/205 |
| 4,801,198 | 1/1989 | Heacock | 351/214 |
| 5,007,729 | 4/1991 | Erickson et al. | 351/219 |
| 5,189,450 | 2/1993 | Crossman et al. | 351/219 |
| 5,200,773 | 4/1993 | Volk | 351/219 |
| 5,309,187 | 5/1994 | Crossman et al. | 351/219 |

FOREIGN PATENT DOCUMENTS

| | | | |
|---|---|---|---|
| 124502 | 5/1984 | European Pat. Off. | 351/219 |
| 2136927 | 12/1972 | France . | |
| 2248814 | 5/1975 | France | 351/219 |
| 1188326 | 3/1965 | Germany | 42/32 |
| 2246182 | 3/1974 | Germany | 351/219 |
| 2660505C2 | 9/1977 | Germany | 351/219 |
| 2610821 | 12/1977 | Germany . | |
| 2559668 | 5/1979 | Germany . | |
| 2203260 | 10/1988 | United Kingdom . | |

OTHER PUBLICATIONS

Sudarsky, R.D., Volk, D., "Aspherical Objective Lenses as an Aid in Indirect Ophthalmoscopy, A Preliminary Report," Reprinted from *American Journal of Ophthalmology* 47:572–575 (Apr. 1959).

James H. Allen, M.D., *May's Manual of the Diseases of the Eye for Students and General Practitioners*, 24th ed., The Williams & Wilkins Company, Baltimore, 1968, p. 280.

Schlegal, H.J., "Simple Wide-Angle Optics for Split Lamp Microscopy Examinations of the Fundus of the Eye (Panfundoscopy)," *Documenta Ophthalmologica* 26:300–308 (1969).

(List continued on next page.)

*Primary Examiner*—Hung X. Dang
*Attorney, Agent, or Firm*—Christensen, O'Connor, Johnson & Kindness PLLC

[57] ABSTRACT

A contact-type ophthalmic lens for use in diagnosis and laser surgery has a contact lens (14), an entry lens (16), and an intermediate lens (18). The lenses are aligned along their optical axes. The anterior surface of the contact lens has an aspheric surface with a high power. The intermediate lens is a meniscus lens with a concave posterior surface and a convex anterior surface. Both surfaces of the entry lens are convex and aspheric. This combination of lenses provides a very wide field of view, allowing regions of the eye anterior to the equator to be readily viewed in an aerial image focused in a plane (50) anterior to the lens system.

8 Claims, 1 Drawing Sheet

OTHER PUBLICATIONS

Sir Stewart Duke-Elder and David Abrams, System of Ophthalmology, vol. 5, *Ophthalmic Optics and Refraction*, The C.V. Mosby Company, St. Louis, 1970, p. 423.

Pomerantzeff, O., Govignon, J., "Design of a Wide-Angle Ophthalmoscope," *Arch. Opthal.* 86:420–424 (Oct. 1971).

Pomerantzeff, O., "A Lens System for Wide-Angle Fundus Photography," *Ophthalmic Photography* 16:101–108 (Summer 1976).

Pomerantzeff, O., "Theory and Practice of the Equator Plus Camera (EPC)", Conf. Proceedings of International Symposium on Ophthalmological Optics (May 7–9, 1978) 117–118.

Pomerantzeff, O., Webb, R.H., Delori, F.C., "Image Formation in Fundus Cameras," *Invest. Ophthalmol. Visual Sci.* 18:630–637 (Jun. 1979).

Pomerantzeff, O., "Wide-Angle Noncontact and Small-Angle Contact Cameras," *Invest. Ophthalmol. Visual Sci.* 19:973–979 (Aug. 1980).

Charles, L. Schepens, M.D., *Retinal Detachment and Allied Diseases*, W.B. Saunders Company, Philadelphia, 1983, Ch. 43, "New and Improved Diagnostic and Surgical Procedures," pp. 1107–1155.

P. Roussel et al., "Contact Glass for Use . . . Optical Aspects," *International Ophthalmology* 6:183–190 (1983).

Dieckert, J.P. et al., "Contact Lenses for Laser Applications," *Ophthalmology: Instrument and Book Supplement* 79–87 (1984).

Arnold Sorsby, Ch. 34, "Biology of the Eye as an Optical System," pp. 1–17.

EXTRA WIDE FIELD OPHTHALMIC LENS

FIELD OF THE INVENTION

The present invention relates to an ophthalmic lens employed in connection with diagnostic and surgical procedures, and more particularly to a compound ophthalmic lens that is utilized for observation of the fundus, particularly the peripheral retina and the portion of the eye at and anterior to the equator, and for delivery of laser energy to all of the same locations.

BACKGROUND OF THE INVENTION

Prior wide field ophthalmic lenses are known in the art. One of these is disclosed in Erickson et al., U.S. Pat. No. 5,007,729 assigned to the assignee hereof. The Erickson et al. patent discloses a three element lens that provides a high quality wide field of view of the fundus and of the peripheral retinal region. It is desirable, however, in many instances to have an even wider field of view so that the region adjacent and anterior to the equator of the eye can be viewed without manipulating the lens position relative to the eye. However, a change in the lens position can only slightly improve the range of view in only a portion of the peripheral portion.

Further increasing the field of view beyond that provided, for example, by the lens of the Erickson et al. patent, requires significant design changes to the lenses, particularly to the entry and intermediate lenses. The rays emanating from the peripheral portions of the eye adjacent and anterior to the equator rays must travel through the crystalline lens, pupil and cornea at even increasing angles relative to the optical axis of the lens. In order to refract these light rays and provide a usable image, all of the lenses, and particularly the entry and intermediate lenses, using prior art design techniques, must be given an ever-increasing diameter. As the diameter of the lens increases so does the overall diameter of the compound system as well as its axial length. Increasing the diameter much beyond that disclosed in the Erickson et al. patent, however, will provide a lens that is impractical to use even though it might be capable of providing a wider field.

SUMMARY OF THE INVENTION

Therefore, other optical techniques have been employed in accordance with the present invention to provide an improved extra wide field ophthalmoscopy contact-type lens. The lens provides very high resolution in the peripheral portions of the image and has a physical size that is substantially equivalent to prior wide angle lenses. The lens provides a field of view that is much larger than prior lenses with no substantial increases in diameter or depth of the lens. The extra wide field ophthalmic lens constructed in accordance with the present invention includes a contact lens, an entry lens and an intermediate lens. All three lenses are located relative to each other on a line substantially coincident with their optical axes. The posterior lens is a contact lens having a posterior and anterior surface. The posterior surface has a curvature approximating the curvature of the cornea and is adapted to contact the cornea. The anterior surface of the contact lens is convex and has a relatively high power. The entry lens is positioned anterior to an spaced from the contact lens. The entry lens has a convex posterior surface and a convex anterior surface. The anterior surface has a power greater than the posterior surface. Both surfaces have a predetermined curvature. The intermediate lens is a meniscus lens and is positioned intermediate the contact lens and the entry lens. The intermediate lens has a concave posterior surface and a convex anterior surface. Each of the surfaces has a predetermined curvature. These lenses in combination receive and refract rays emanating from the fundus of the eye, particularly those from adjacent and anterior to the equator to form a very wide field aerial image of the fundus of the eye anterior to and in close proximity to the anterior surface of the entry lens.

BRIEF DESCRIPTION OF THE DRAWING

A better understanding of the present invention can be derived by reading the ensuing specification in conjunction with the accompanying drawing, wherein.

DETAILED DESCRIPTION OF THE PREFERRED EMBODIMENT

Figure 1:
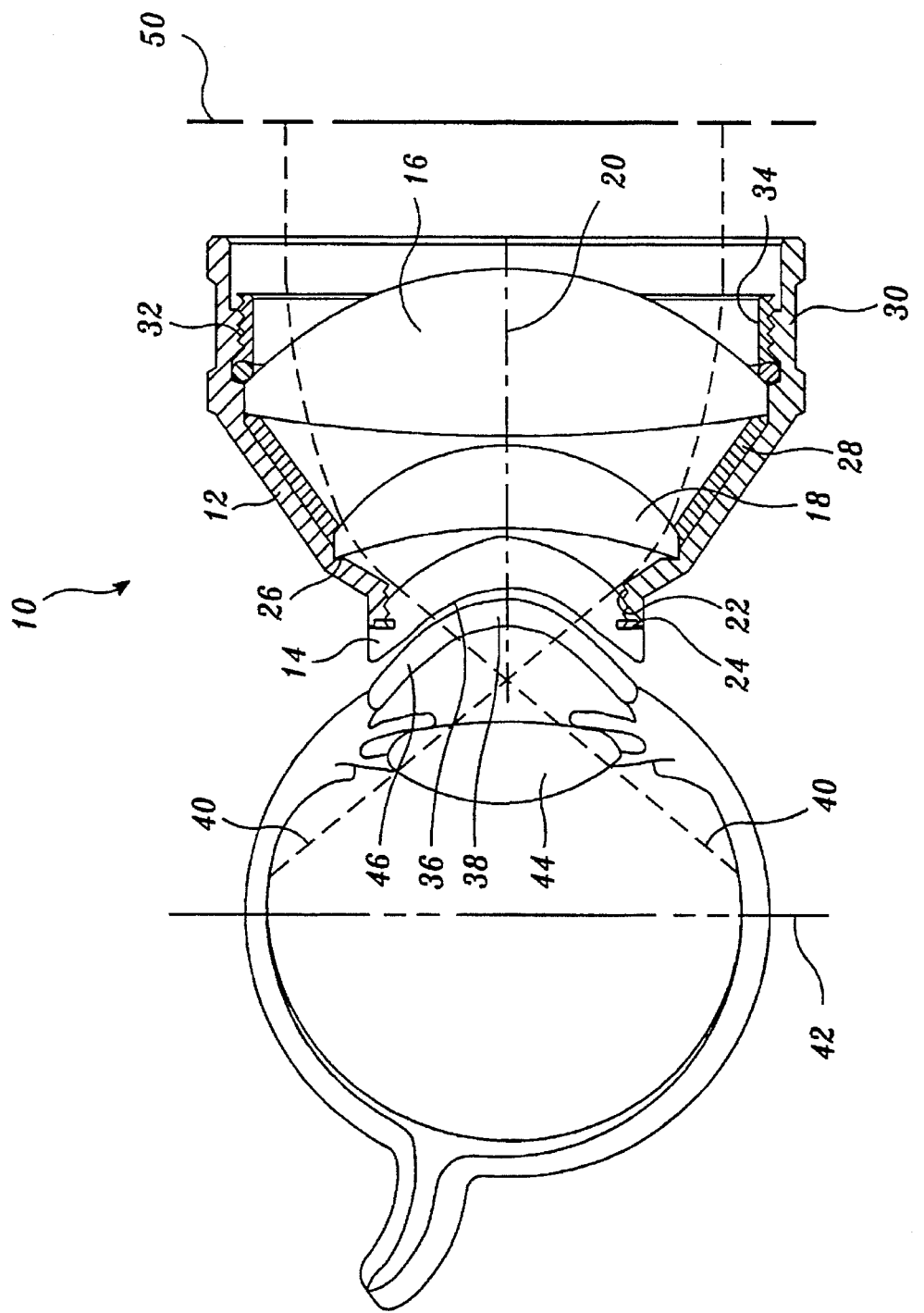
FIG. 1 is a longitudinal sectional view of the lens constructed in accordance with the present invention shown in contact with the cornea of an eye.

Referring first to FIG. 1, the ophthalmic lens system 10 of the present invention comprises a lens holder 12, a contact lens 14, entry lens 16, and an intermediate lens 18. All of the lenses are circular in axial view and are aligned with each other along a common optical axis 20. The contact lens 14 is provided with external threads 22 adjacent its peripheral edge and an anterior facing shoulder 24 located at the posterior end of the threads 22. The lens holder 12 is generally frustoconically shaped with its smallest diameter positioned adjacent the contact lens 14 and its largest diameter positioned anterior to the contact lens 14. The inner diameter of the posterior end of the lens holder 12 carries internal threads that mate with the threads on the contact lens 14. The contact lens 14 is then screwed into the lens holder 12 until the shoulder 24 abuts the posterior edge of the lens holder 12.

The intermediate lens 18 has a larger diameter than the contact lens 14. A lens receiving groove 26 is provided in the central portion of the lens holder 12 and receives the intermediate lens 18. A frustoconically shaped spacer 28 has a shape similar to the frustoconically shaped portion of the lens holder 12. The posterior end of the spacer 28 rests adjacent the outer periphery of the intermediate lens 18 and extends in an anterior and outward direction from that location. The entry lens 16 has a larger diameter than the intermediate lens 18 and fits within the lens holder 12 such that the outer periphery abuts the anterior edge of the spacer 28. The anterior end of the lens holder 12 carrier a cylindrical section 30 having internal threads 32. The cylindrical section 30 extends forwardly from the location of the entry lens 16. A retaining ring 34 having external threads mates with the threads 32 on the cylindrical section 30 to hold the entire lens system in place.

The lens in use is positioned in juxtaposition to the eye so that the posterior surface 36 of the contact lens 14 is placed in contact with the anterior surface of the cornea 38. A coupling fluid such as water or other suitable material known in the art can be used to provide an optical couple between the cornea 38 and the contact lens 14. Light rays 40 indicated by dashed lines emanating from a position anterior to the equator of the eye, indicated by dashed line 42, travel through the crystalline lens 44, the pupil of the eye and the cornea 38, and enter the contact lens 14. The rays 40 are then refracted by the anterior surface of the contact lens 14 and the posterior and anterior surfaces of both the intermediate lens 18 and entry lens 16 in such a manner that they form an aerial image at plane 50 anterior but in close proximity to the anterior portion of the lens holder 12. Of course, light rays emanating from points between the rays 40 across the entire fundus of the eye are also directed through the lens system to help form a complete image at plane 50.

In accordance with the present invention, the posterior and anterior surfaces of the contact, intermediate, and entry lenses 14, 18, and 16 have predetermined curvatures. In the most preferred embodiment, the posterior and anterior surfaces of the entry lens 16 and the anterior surface of the contact lens 14 are aspheric while the posterior surface of the contact lens and both surfaces of the intermediate lens 18 are spherical. In the preferred embodiment of the invention, the posterior surface of the contact lens 14 is concave and conforms substantially to the shape of the cornea 38. The anterior surface of the contact lens 14 is preferably convex and in accordance with the present invention has a relatively high power. The intermediate lens 18 is a meniscus lens with a concave posterior surface and a convex anterior surface. Finally, both surfaces of the entry lens 16 are convex. To provide optimum performance, however, the power of the anterior surface is significantly greater than that of the posterior surface over the entire radial extent of the anterior surface of the entry lens 16 as shown in FIG. 1. These lens shapes and their respective powers allow the lens constructed in accordance with the present invention to intercept light rays from a location more anterior in the eye than had previously been thought possible.

The aspheric surfaces of the contact and entry lenses are defined by the formula:

$$Z = \frac{CK^2}{1 + \sqrt{1 - C^2 EK^2}} + A_4 K^4 + A_6 K^6 + A_8 K^8 + \ldots \quad (1)$$

wherein $C = (1/R)$, $E = b + 1$, $K^2 = x^2 + y^2$, $A_n$ are higher order aspheric constants, and wherein Z is in the direction of the optical axis of the lens and x and y are orthogonal thereto. When R is positive a convex surface results, and when R is negative a concave surface results.

The values for R, b, thickness (t) diameter (d) and index of refraction (n) can vary with prescribed parameters while yielding acceptable image quality. The preferred and most preferred values for the design parameters of the lenses are set forth below. The "1" subscript indicates an anterior surface while the "2" indicates a posterior surface. Where no conic constant (b) is indicated, R represents the spherical radius of curvature of the surface.

| Contact | Preferred | Most Preferred |
|---|---|---|
| $R_1$ | 4.27 to 7.93 mm | 6.10 ± 0.31 mm |
| $b_1$ | −5 to 0 | −1.244 ± 0.062 |
| $R_2$ | −9.0 to −6.0 mm | −7.45 ± 0.37 mm |
| t | .75 to 4.53 mm | 2.74 ± 0.15 mm |
| n | 1.44 to 1.97 | 1.49 ± 0.01 |
| d | 13.0 to 21.0 mm | 17.1 ± 0.2 mm |

| Intermediate | Preferred | Most Preferred |
|---|---|---|
| $R_1$ | 8.75 to 16.25 mm | 12.50 ± 0.63 mm |
| $R_2$ | −39.00 to −21.00 mm | −30.00 ± 1.50 mm |
| t | 3.32 to 6.68 mm | 5.0 ± 0.2 mm |
| n | 1.44 to 1.97 | 1.71 ± 0.01 |
| d | 17.0 to 25.0 mm | 21.0 ± 0.2 mm |

| Entry | Preferred | Most Preferred |
|---|---|---|
| $R_1$ | 10.47 to 19.44 mm | 14.95 ± 0.75 mm |
| $b_1$ | −10 to 0 | −1.929 ± 0.096 |
| $R_2$ | 49.16 to 91.29 mm | 70.23 ± 3.51 mm |
| $b_2$ | −16 to 0 | −8.782 ± 0.439 |
| t | 6.5 to 14.5 mm | 10.0 ± 0.2 mm |
| n | 1.44 to 1.97 | 1.81 ± 0.01 |
| d | 27.0 to 35.0 mm | 31.0 ± 0.2 mm |

By constructing a lens in accordance with the present invention, an extra wide field can be achieved in a manner heretofore not available and in a manner not suggested by prior lenses. Specifically, the lens design of the present invention brings the power of the lens system very close to the eye, almost as close as is possible within the physical constraints of the system. Moreover, a well-corrected entrance pupil is provided by the lens system when used in conjunction with an ophthalmic microscopic. The lens is designed so that all of the chief rays of the optical system will pass near the center of the entrance pupil of the system. The entrance pupil of the lens system of the present invention is also positioned very close to the patient's pupil. As a consequence, the chief rays are not scattered axially relative to the entrance pupil as in prior lenses, helping to achieve the desired result of a very wide field. These results are achieved primarily by increasing the power of the posterior surface of the contact lens and by introducing a meniscus lens into the system as the center element. These physical features along with the combination and power and design of the entry lens system provides a result heretofore unobtainable.

The present invention has been described in conjunction with a preferred embodiment and variations thereof. It will be understood by one of ordinary skill, however, that various alterations, changes and substitutions of equivalents can be made without departing from the broad concepts disclosed here. It is therefore intended that the present invention be limited only by the definition contained in the appended claim and the equivalents thereof.

The embodiments of the invention in which an exclusive property or privilege is claimed are defined as follows:

1. A contact-type ophthalmic lens for use in diagnosis and treatment of the eye comprising:

a contact lens having a posterior surface and an anterior surface, the posterior surface having a curvature approximating the curvature of the cornea and adapted to contact the cornea, the anterior surface being convex and having a relatively high power, an entry lens positioned anterior to and substantially coincident with the optical axis of the contact lens, the entry lens having a convex posterior surface and a convex anterior surface, both the anterior surface and the posterior surface having a predetermined curvature, the anterior surface of the entry lens having a power significantly greater than the posterior surface over its entire radial extent, and an intermediate meniscus lens positioned intermediate the contact lens and the entry lens and positioned substantially coincident with the optical axis of the contact lens, the intermediate lens having a concave posterior surface and a convex anterior surface, each of the surfaces having a predetermined curvature, the lenses in combination receiving and refracting rays emanating from the fundus of the eye, including regions anterior to the equator of the eye, to form a very wide field, aerial image of the fundus of the eye anterior to and in close proximity to the anterior surface of the entry lens.

2. The lens of claim 1 wherein the anterior surface of the contact lens has a relatively high power.

3. The lens of claim 2 wherein the anterior surface of the entry lens has a power greater than the posterior surface.

4. The lens of claim 3 wherein the anterior surface of the contact lens is aspheric.

5. The lens of claim 4 wherein the anterior and posterior surfaces of the entry lens are aspheric.

6. The lenses of claim 5 wherein the aspheric surfaces are defined by the formula:

$$Z = \frac{CK^2}{1 + \sqrt{1 - C^2 E K^2}} + A_4 K^4 + A_6 K^6 + A_8 K^8 + \ldots \quad (1)$$

wherein
$C = (1/R)$,
$E = b + 1$,
$K^2 = x^2 + y^2$,
$A_n$ are higher order aspheric constants, and
wherein Z is in the direction of the optical axis of the lens and x and y are orthogonal thereto. When R is positive a convex surface results, and when R is negative a concave surface results.

7. A contact-type ophthalmic lens for use in diagnosis and treatment of the eye comprising:

a contact lens having a posterior surface and an anterior surface, the posterior surface having a curvature approximating the curvature of the cornea and adapted to contact the cornea, the anterior surface being convex and aspheric and having a relatively high power, an entry lens positioned anterior to and substantially coincident with the optical axis of the contact lens, the entry lens having a convex aspheric posterior surface and a convex aspheric anterior surface, both the anterior surface and the posterior surface having a predetermined curvature, the anterior surface of the entry lens having a power greater than the posterior surface, an intermediate meniscus lens positioned intermediate the contact lens and the entry lens and positioned substantially coincident with the optical axis of the contact lens, the intermediate lens having a concave posterior surface and a convex anterior surface, each of the surfaces having a predetermined curvature, the lenses in combination receiving and refracting rays emanating from the fundus of the eye to form a very wide field, aerial image of the fundus of the eye anterior to and in close proximity to the anterior surface of the entry lens, wherein the aspheric surfaces are defined by the formula;

$$Z = \frac{CK^2}{1 + \sqrt{1 - C^2 E K^2}} + A_4 K^4 + A_6 K^6 + A_8 K^8 + \ldots \quad (1)$$

wherein
$C = (1/R)$,
$E = b + 1$,
$K^2 = x^2 + y^2$,
$A_n$ are higher order aspheric constants, and
wherein Z is in the direction of the optical axis of the lens and x and y are orthogonal thereto, when R is positive a convex surface results, and when R is negative a concave surface results, and wherein the R, b, thickness (t), diameter (d) and index of refraction (n) for the lenses have the following values:

for the contact lens
$R_1$ equals 4.27 to 7.93 mm,
$b_1$ equals −5 to 0,
$R_2$ equals −9.0 to −6.0 mm,
t equals 0.75 to 4.53 mm,
n equals 1.44 to 1.97, and
d equals 13.0 to 21.0 mm, for the intermediate lens
$R_1$ equals 8.75 to 16.25 mm,
$R_2$ equals −39.0 to −21.0 mm,
t equals 3.32 to 6.68 mm,
n equals 1.44 to 1.97, and
d equals 17.0 to 25.0 mm, for the entry lens
$R_1$ equals 10.47 to 19.44 mm,
$b_1$ equals −10 to 0,
$R_2$ equals 49.16 to 91.29 mm,
$b_2$ equals −16 to 0,
t equals 6.5 to 14.5 mm,
n equals 1.44 to 1.97, and
d equals 27.0 to 35.0 mm.

8. The lens of claim 7 wherein the R, b, thickness (t), diameter (d) and index of refraction (n) for the lenses have the following values:

for the contact lens
$R_1$ equals 6.10±0.31 mm,
$b_1$ equals −1.244±0.062,
$R_2$ equals −7.45±0.37 mm,
t equals 2.74±0.15 mm,
n equals 1.49±0.01, and
d equals 17.1±0.2 mm, for the intermediate lens
$R_1$ equals 12.50±0.63 mm,
$R_2$ equals −30.0±1.5 mm,
t equals 5.0±0.2 mm,
n equals 1.71±0.01, and
d equals 21.0±0.2 mm for the entry lens
$R_1$ equals 14.95±0.75 mm,
$b_1$ equals −1.929±0.096,
$R_2$ equals 70.23±3.51 mm,
$b_2$ equals −8.782±0.439,
t equals 10.0±0.2 mm,
n equals 1.81±0.01, and
d equals 31.0±0.2 mm.

* * * * *